(12) United States Patent
Simon (10) Patent No.: US 10,034,993 B2
(45) Date of Patent: Jul. 31, 2018

(54) AIRWAY OXYGENATOR

(71) Applicant: Gary Simon, London (GB)

(72) Inventor: Gary Simon, London (GB)

( * ) Notice: Subject to any disclaimer, the term of this patent is extended or adjusted under 35 U.S.C. 154(b) by 1068 days.

(21) Appl. No.: 14/254,403

(22) Filed: Apr. 16, 2014

(65) Prior Publication Data

US 2014/0309545 A1 Oct. 16, 2014

Related U.S. Application Data

(60) Provisional application No. 61/812,287, filed on Apr. 16, 2013.

(51) Int. Cl.
| | | |
|---|---|---|
| *A61M 16/04* | (2006.01) | |
| *A61B 5/08* | (2006.01) | |
| *A61B 5/083* | (2006.01) | |

(52) U.S. Cl.
CPC ......... *A61M 16/0486* (2014.02); *A61B 5/082* (2013.01); *A61M 16/04* (2013.01); *A61M 16/0461* (2013.01); *A61B 5/0836* (2013.01); *A61M 16/0418* (2014.02); *A61M 16/0488* (2013.01); *A61M 2202/0007* (2013.01); *A61M 2202/0208* (2013.01); *A61M 2205/18* (2013.01); *A61M 2230/432* (2013.01)

(58) Field of Classification Search
CPC .............. A61M 16/0486; A61M 16/04; A61M 16/0461; A61M 16/0418; A61M 16/0488; A61M 2202/0007; A61M 2202/0208; A61M 2205/18; A61M 2230/432; A61B 5/082; A61B 5/0836
See application file for complete search history.

(56) References Cited

U.S. PATENT DOCUMENTS

| | | | | |
|---|---|---|---|---|
| 3,915,173 | A * | 10/1975 | Brekke | A61B 17/12022 128/207.15 |
| 5,166,990 | A * | 11/1992 | Riccitelli | A61B 5/0084 385/117 |
| 6,098,617 | A * | 8/2000 | Connell | A61M 16/04 128/200.26 |
| 2005/0279360 | A1* | 12/2005 | Wei | A61M 16/04 128/207.14 |
| 2010/0269830 | A1* | 10/2010 | Layer | A61M 1/008 128/205.27 |
| 2011/0023871 | A1* | 2/2011 | Pacey | A61M 16/04 128/200.26 |
| 2012/0080037 | A1* | 4/2012 | Guyuron | A61M 16/0461 128/207.18 |

* cited by examiner

*Primary Examiner* — Gregory Anderson
*Assistant Examiner* — Jonathan Paciorek
(74) *Attorney, Agent, or Firm* — Blake, Cassels & Graydon LLP; Brett J. Slaney; John R. S. Orange (57) ABSTRACT

An airway device for use with deep sedation has a pair of conduits, one to supply oxygenated gas and the other to extract exhaled gas. The conduits are encompassed in a permeable sleeve with a stylet to facilitate positioning of the device in the airway.

22 Claims, 6 Drawing Sheets

AIRWAY OXYGENATOR

CROSS-REFERENCE TO RELATED APPLICATIONS

This application claims priority from U.S. Provisional Application No. 61/812,287 filed Apr. 16, 2013; the entire contents of which is incorporated herein by reference.

FIELD OF THE INVENTION

The present invention relates to methods and apparatus for facilitating surgical procedures performed under deep sedation.

BACKGROUND

Most surgical procedures require some form of intervention to alleviate pain and/or discomfort and/or stress for the patient. Dental procedures such as dental operations are recognized as potentially highly stressful for the patient and this can be exacerbated when the patient is a younger person or child. In some situations, the stress induced by the procedure is sufficient to impair the ability of the dentist or dental surgeon to perform the procedure and may be sufficiently traumatic for the patient that further procedures will not be contemplated.

To overcome the difficulties in performing the dental procedure, it is sometimes necessary to resort to the use of anesthetics for dental procedures, such as removing the wisdom teeth, or for patients who are highly stressed or to treat younger children.

Deep sedation is now frequently performed in hospitals for out of operating procedures that are painful or require lack of movement. Deep sedation is also used in out of hospital settings which would include pediatric dental offices. Anesthetic machine (delivering anesthetic gases) is not needed for deep sedation anesthesia. However the monitoring would be similar for both—the difference being the lack of need to monitor inhaled and exhaled anesthetic gases for those patients receiving deep sedation. There is however a reticence to the use of deep sedation with dental procedures because of historical issues regarding substandard monitoring, inadequate training and distraction resulting from the dentist taking responsibility for the procedure and the anesthesia.

The monitoring of the patient condition includes the maintenance of the level of oxygen in the blood and the continuous monitoring of the patients breathing. Monitoring of the patients breathing, includes monitoring the carbon dioxide exhaled by the patient. Nasal prongs are typically used for such monitoring, but with dental procedures they may be unreliable due to the fact that breathing may take place through the open mouth, the nasal passages or both. These concerns are exaggerated in children who have proportionally smaller nasal passages that may be partially occluded by adenoids or secretions.

A further difficulty associated with the supply of oxygen and monitoring of the patient arises from the need to perform the procedure within the mouth so that there is a risk that the oxygen supply and carbon dioxide monitoring apparatus will impinge upon the area in which the dental surgeon may wish to work.

It is therefore an object of the present invention to provide an apparatus and method in which the above disadvantages are obviated or mitigated.

SUMMARY OF THE INVENTION

In general terms, the present invention provides an airway device having a pair of gas conduits, one to supply oxygen and the other to receive carbon dioxide. The conduits terminate within a porous sleeve and a malleable stylet allows positioning of the device to maintain the desired location of the sleeve.

In the preferred embodiment, the sleeve is effective to distribute the oxygen within the airway of the patient and to receive carbon dioxide expelled by the patient. The sleeve spaces the conduits from the sidewall of the patient's oropharynx and avoids direct impingement of the oxygen supply with the surrounding wall and thereby avoids subcutaneous injection of the oxygen.

In a further aspect there is provided a method of monitoring the condition of a patient during sedation by providing a supply of oxygen to the patient through a first conduit, monitoring carbon dioxide delivered through a second conduit, maintaining the first and second conduits in spaced relationship from the patients oropharynx by encompassing the conduits in a sleeve, and maintaining the position of the sleeve using a malleable stylet.

BRIEF DESCRIPTION OF THE DRAWINGS

Embodiments of the invention will now be described by way of an example only with reference to the accompanying drawings in which.

DETAILED DESCRIPTION OF THE INVENTION

Figure 1:
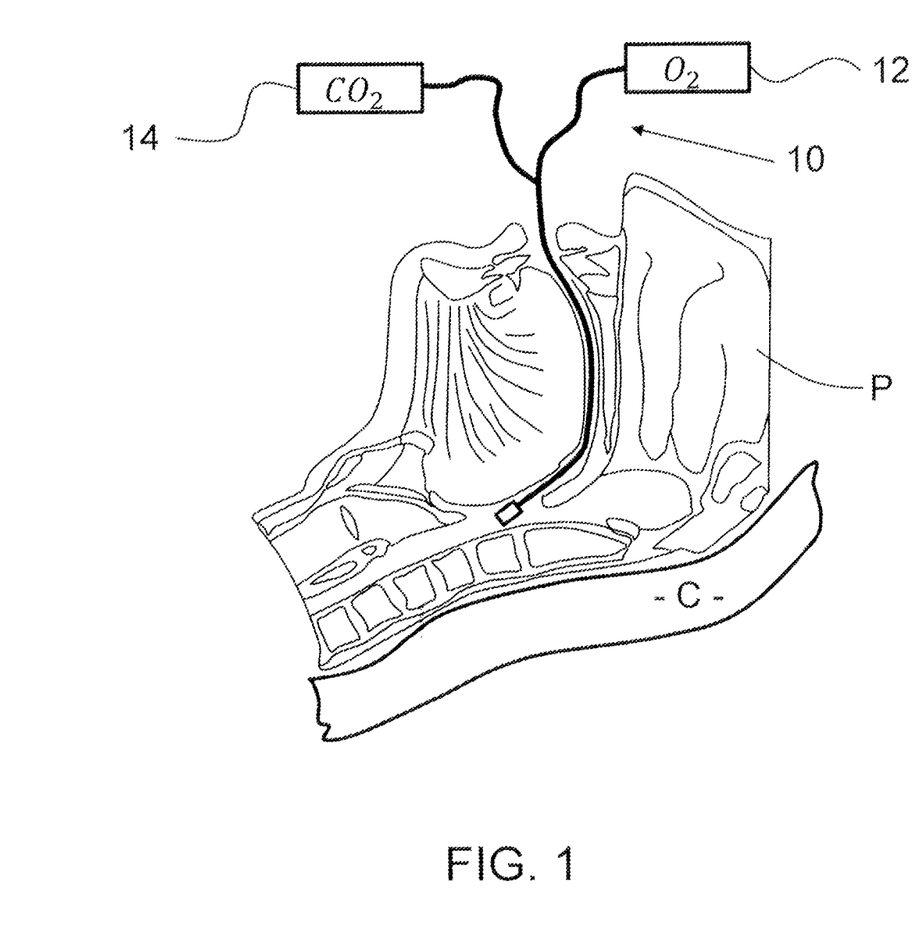
FIG. 1 is a schematic representation of a patient undergoing a surgical procedure.

Referring therefore to FIG. 1, a patient indicated at P is supported on a dental chair or operating table C to undergo a dental procedure. The patient P is sedated using an intravenous injection and an airway oxygenator 10 inserted into the patients mouth to monitor the patient's condition at the back of the mouth adjacent to the patients oropharynx. An oxygen supply 12 is connected to an airway oxygenator 10 to deliver oxygen to the patient and a carbon dioxide monitor 14 is connected to the probe to monitor the carbon dioxide levels in air expelled by the patient.

Figure 2:
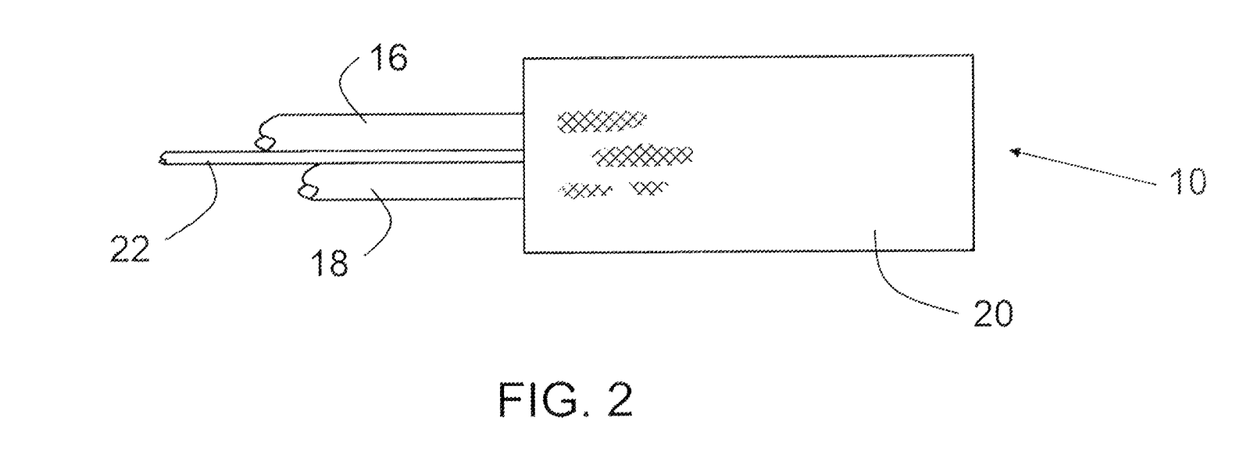
FIG. 2 is a side view of a dental probe.
Figure 3:
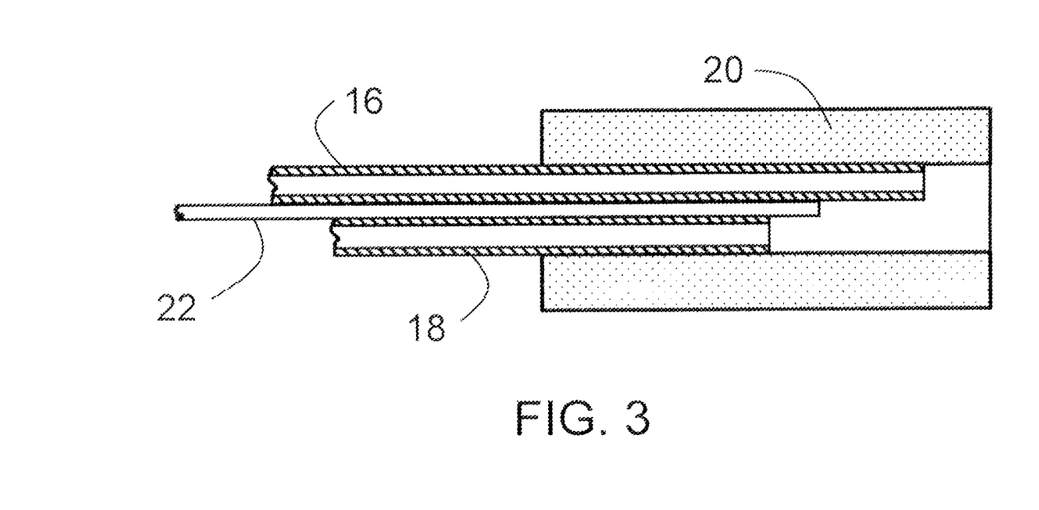
FIG. 3 is a section of the probe of FIG. 2.
Figure 4:
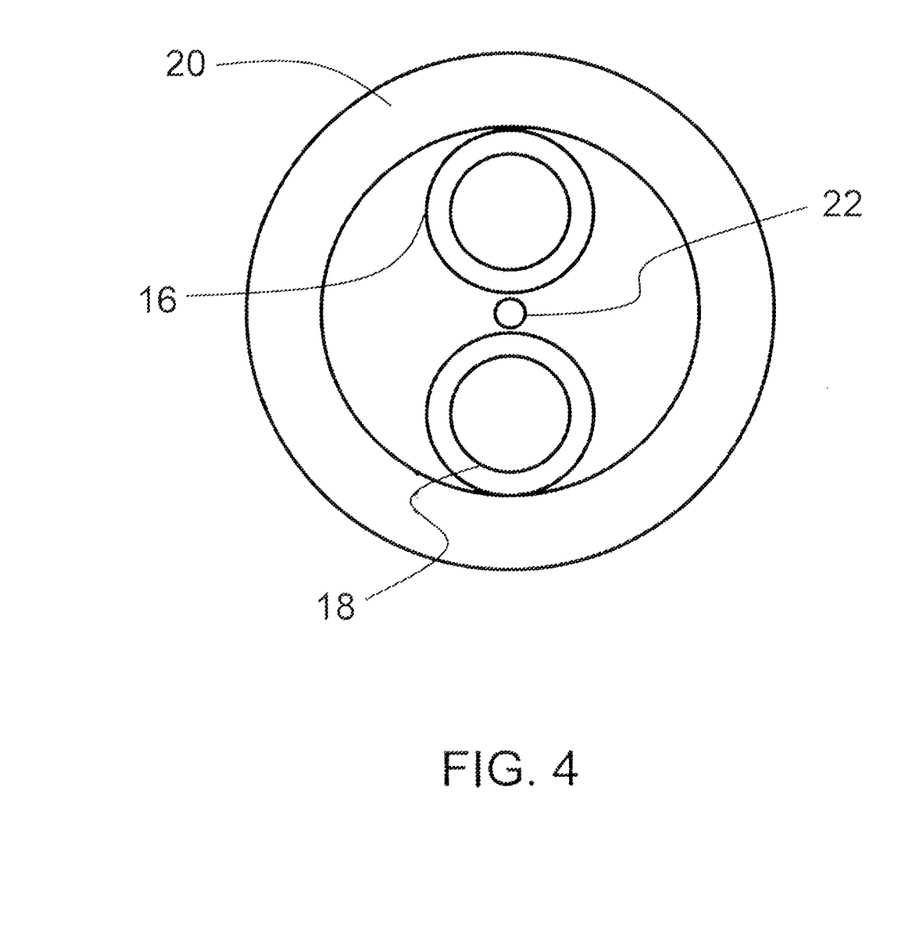
FIG. 4 is an end view of the probe of FIG. 3.

As can best be seen in FIGS. 2-4, the airway oxygenator 10 has a pair of conduits 16, 18 that are connected respectively through the oxygen supply 12 and the $CO_2$ monitor 14. The conduits 16, 18 are typically lumens made from a flexible plastics material and having an internal diameter in the order of 2 mm, capable of delivering an oxygen stream to the patient in the order of 1-3 liters per minute.

The conduits 16, 18 terminate in a sleeve 20 so that the ends of the conduits 16, 18 are enclosed by the sleeve. As can be seen in FIG. 3, the termination of the conduits 16, 18 are staggered in the longitudinal direction with the conduit 16 connected to the oxygen supply extending beyond the termination of the conduit 18 connected to the carbon dioxide monitor. The ends can be coterminous if preferred.

The sleeve 20 is permeable and typically is formed from a porous soft material, such as an open cell foam to allow the free passage of gas through the sleeve. The sleeve 20 is sufficiently resilient to maintain a spacing between the conduits 16, 18 and the internal surface of the mouth or oropharynx. The sleeve 20 will typically have free body dimensions of 9 mm diameter and 25 mm length, and an internal diameter to receive snugly the conduits 16, 18. The sleeve is secured to the conduits 16, 18, by adhesive or laser welding to prevent separation in use.

Located between the conduit 16, 18 is a stylet 22 that is bonded or connected to each of the conduits 16 over several inches, sufficient for the stylet to extend outside the mouth. The stylet 22 is a malleable material such as a wire formed from a biocompatible material and has sufficient bending stiffness to resist any bias exerted by the conduits 16, 18.

The stylet 22 and conduits 16, 18 are inter-connected as a unitary body over at least several inches to ensure compact placement within the patient.

In Use, the oxygenator 10 is connected to the oxygen supply 12 and the $CO_2$ monitor 14 via the conduit 16, 18 and the sleeve 20 located on the terminal portion of the probe 10. The oxygenator 10 may then be inserted into the patient's mouth and the malleable stylet 22 adjusted so that the sleeve 20 is located in the optimum position within the patients mouth. The stylet 22 maintains the conduit 16, 18 in the required position adjacent to the oropharynx and the sleeve 20 is effective to maintain the conduit 16, 18 in spaced relationship to the mouth of the patient.

Oxygen delivered through the conduit 16, permeates through the sleeve 20 to be available for the patient, and the gas expelled by the patient during normal breathing is collected in the conduit 18 and processed by the $CO_2$ monitor. The $CO_2$ monitor will ensure that there is an expected level of $CO_2$ in the collected gas which is used as an indication of satisfactory breathing of the patient. In the event that an abnormal level is noted, an alarm alerts the anesthesiologist to the adverse condition.

The resilient material of the sleeve 20 prevents damage to the patients mouth and avoids direct contact of the oxygen conduit 16 with the patients to avoid subcutaneous injection of the oxygen.

Upon completion of the dental procedure, the probe may simply be removed from the patient and discarded for hygienic reasons.

If during the procedure it is necessary to reposition the probe, the stylet 22 may be reconfigured to move the probe into a different portion of the patient's mouth, allowing the surgeon to continue with the procedure.

Figure 5:
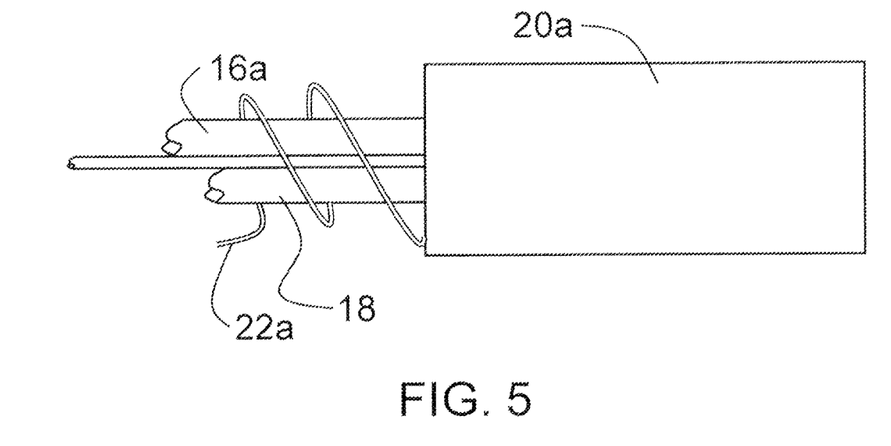
FIG. 5 is a view, similar to FIG. 2, of an alternative embodiment of probe.

As shown in FIG. 3, the stylet 22 is formed as a single wire that is coextensive with and connected to each of the conduits 16, 18. An alternative configuration is shown in FIG. 5 in which like reference numerals will be used to denote like components with a suffix a added for clarity. In the embodiment of FIG. 5, the conduits 16a, 18a are located within the sleeve 20a and a stylet 22a is wound about the pair of conduits in a generally helical configuration. The stylet contains the conduit within the confines of the helical winding and provides the necessary rigidity to maintain the conduits in the required location. In this manner, the stylet may be wound for varying extents along the conduits, 16, 18 to suite the particular operating environment.

Figure 6:
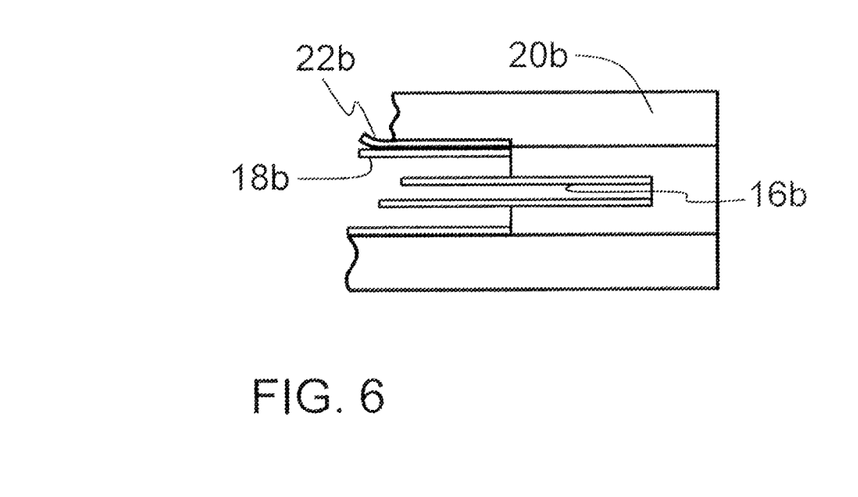
FIG. 6 is a view, similar to FIG. 3, of a still further embodiment of probe.
Figure 7:
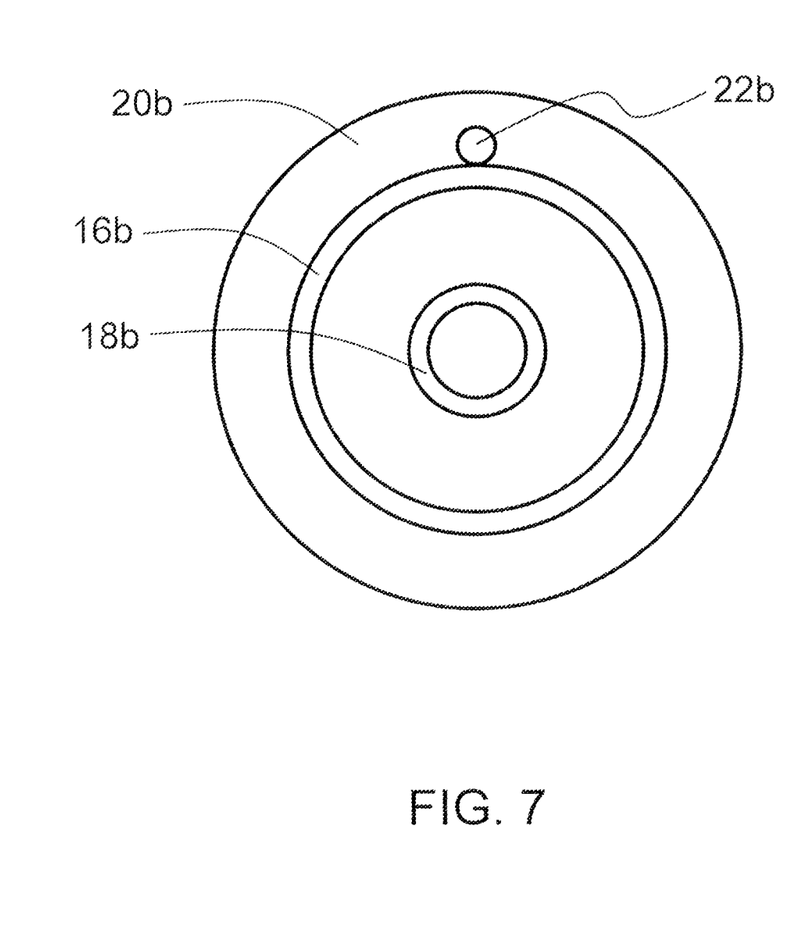
FIG. 7 is an end view of the probe of FIG. 6.

A further embodiment is shown in FIGS. 6 and 7 where like components will be designated by a like reference number with a suffix b added for clarity. In the embodiment of FIGS. 6 and 7, the conduits 16, 18 are arranged coaxially with the conduit 16b extending beyond the termination of the conduit 18b. The stylet 22b may be connected to the outer surface of the conduit 18b, as shown above with respect to the embodiment of FIGS. 2-4, or may be wound about the outer body of the conduit 18b as shown above with respect to FIG. 5.

Figure 8:
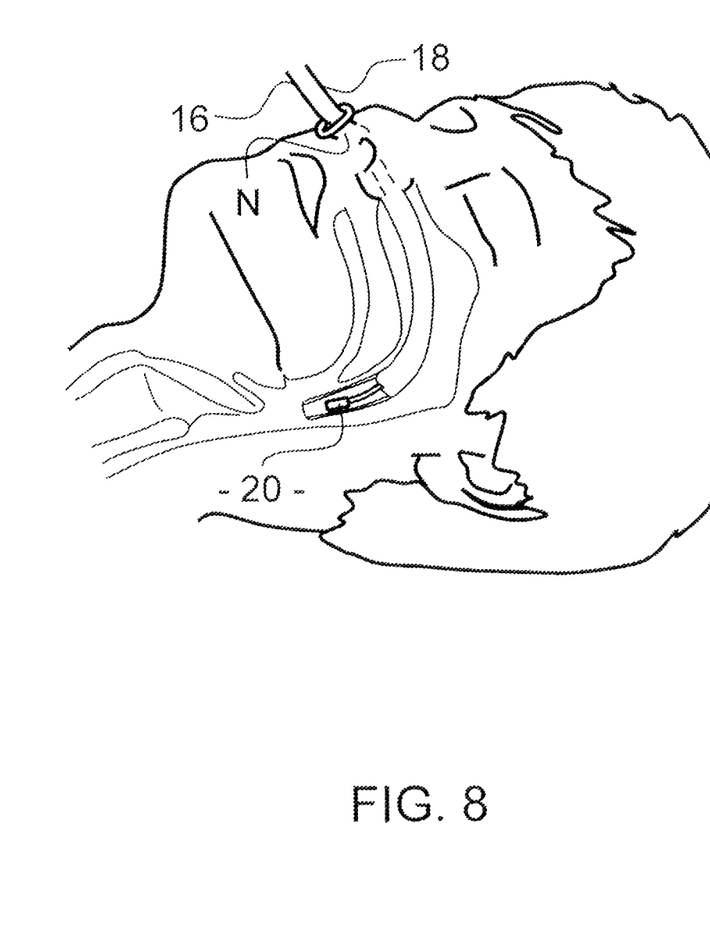
FIG. 8 is a view similar to FIG. 1 of an alternative surgical procedure.

As shown in FIG. 8, the airway oxygenator 10 may also be used with nasopharyngeal airways, indicated at N. The nasopharyngeal airways N are inserted into the nostril of the deeply sedated patient to provide a clear passage for the patient to breath.

The airway oxygenator 10 is inserted in to the nasopharyngeal airway N and positioned adjacent the distal end of the nasopharyngeal airway. The airway oxygenator 10 is dimensioned to suit the nasopharyngeal airway. The sleeve 20 typically has a diameter of 3 mm and length of 20 mm for use with a 4-6 nasopharyngeal airway and 6 mm diameter and 20 mm length when used with a 7-9 nasopharyngeal airway.

In each case, the airway oxygenator does not completely occlude the nasopharyngeal airway and the porous sleeve allows flow along the airway as well as distribution of oxygen in to the region of the oropharynx.

It will be seen from the above description that an airway oxygenator is provided in which oxygen is delivered to the required location without inhibiting access to the mouth and facial regions and carbon dioxide may be monitored during the surgical procedure. The provision of the porous sleeve 22 ensures diffusion of the oxygen supplied whilst maintaining the conduits 16, 18 in spaced relationship to the patient's oropharynx.

The invention claimed is:

1. An airway device, the device comprising:
a first conduit for transmitting a supply of oxygenated gas to a subject's airway;
a second conduit for receiving exhaled gas from the subject's airway;
a stylet coupled to the first and second conduits for positioning the device in a desired position relative to the subject's airway; and
a sleeve sized for receiving terminal portions of the first and second conduits and extending radially beyond said conduits to space the first and second conduits from the subject's airway, the sleeve being permeable to the supplied and exhaled gases.

2. The airway device of claim 1, wherein the sleeve is sized to space the first and second conduits from a sidewall of the subject's oropharynx, thereby inhibiting subcutaneous injection of the oxygenated gas.

3. The airway device of claim 1, wherein the device is configured to be inserted into the subject orally or nasopharyngeally and positionable at the back of the subject's mouth adjacent to the subject' oropharynx.

4. The airway device of claim 1, further comprising a carbon dioxide monitor coupled to the second conduit to monitor carbon dioxide in the exhaled gas.

5. The airway device of claim 1, wherein the first and second conduits are flexible lumens having an internal diameter of 2 mm.

6. The airway device of claim 1, wherein the sleeve is sufficiently resilient to maintain the spacing between the conduits and the subject's airway.

7. The airway device of claim 1, wherein the sleeve has an internal diameter to receive snugly the first and second conduits.

8. The airway device of claim 1, wherein the sleeved is secured to the conduits to prevent separation during use.

9. The airway device of claim 1, wherein the stylet is malleable and has sufficient bending stiffness to resist any bias exerted by the conduits.

10. The airway device of claim 1, wherein the stylet is configured to connect the first and second conduits as a unitary body over at least several inches of the length of the probe.

11. The airway device of claim 1, wherein the stylet is coextensive with and connected to each of the conduits.

12. The airway device of claim 1, wherein the stylet is wound about the first and second conduits in a helical configuration.

13. The airway device of claim 1, wherein the first and second conduits are arranged adjacent to one another, the first conduit terminal end extending beyond the terminal end of the second conduit or being coterminous with the terminal end of the second conduit.

14. The airway device of claim 1, wherein the first and second conduits are arranged coaxially with respect to one another, the first conduit terminal end extending beyond the terminal end of the second conduit.

15. The airway device of claim 1, wherein the airway device is sized to not completely occlude the airway.

16. The airway device of claim 1, wherein the airway device is sized to permit access to mouth and facial regions of the subject.

17. A method of supporting respiration of a subject, the method comprising:
   positioning a terminal portion of an airway device within the subject's airway, the terminal portion of the airway device being in gaseous communication with the subject's airway;
   supporting said airway device within the subjects airway using a resilient sleeve disposed on a terminal portion of the airway device, the sleeve being permeable to the oxygenated and exhaled gases to space said terminal portion from the subject's airway to prevent subcutaneous oxygenation of the airway;
   maintaining the position of the airway device with respect to the subject's airway;
   providing oxygenated gas to the patient through a first conduit disposed in the airway device, the first conduit terminating in the terminal portion of the airway device; and
   monitoring carbon dioxide produced by the subject using the airway device by:
      collecting gas exhaled by the subject using a second conduit disposed in the airway device; and
      quantifying carbon dioxide in the exhaled gas;
   thereby supporting respiration of the subject.

18. The method of claim 17, wherein the positioning step comprises positioning the terminal portion of the airway device at the back of the subject's mouth, adjacent to, and spaced from, the subject's oropharynx wall.

19. The method of claim 18, wherein the positioning step comprises inserting the airway device through the subject's mouth or nasopharynx.

20. The method of claim 17, wherein the provision of oxygenated gas and collection of exhaled gas do not block the subject's airway.

21. The method of claim 17, wherein the subject is undergoing sedation.

22. The method of claim 17, wherein the subject is undergoing oral surgery.

* * * * *

UNITED STATES PATENT AND TRADEMARK OFFICE
CERTIFICATE OF CORRECTION

PATENT NO.         : 10,034,993 B2
APPLICATION NO.    : 14/254403
DATED              : July 31, 2018
INVENTOR(S)        : Gary Simon Page 1 of 1

It is certified that error appears in the above-identified patent and that said Letters Patent is hereby corrected as shown below:

On the Title Page

At items (71) and (72), the Applicant and Inventor's country of residence should read as "CA".

Signed and Sealed this
Eleventh Day of September, 2018

Andrei Iancu
*Director of the United States Patent and Trademark Office*